United States Patent
Li et al.

(10) Patent No.: US 10,662,452 B2
(45) Date of Patent: May 26, 2020

(54) STRAIN OF MEYEROZYMA GUILLIERMONDII AND ITS USE IN METHODS OF CATALYTIC SYNTHESIS OF 2,5-DIHYDROXYMETHYLFURAN

(71) Applicant: SOUTH CHINA UNIVERSITY OF TECHNOLOGY, Guangzhou (CN)

(72) Inventors: Ning Li, Guangzhou (CN); Yanmei Li, Guangzhou (CN); Minhua Zong, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 0 days.

(21) Appl. No.: 16/083,510

(22) PCT Filed: Dec. 15, 2016

(86) PCT No.: PCT/CN2016/110022
§ 371 (c)(1),
(2) Date: Sep. 9, 2018

(87) PCT Pub. No.: WO2018/040372
PCT Pub. Date: Mar. 8, 2018

(65) Prior Publication Data
US 2019/0040430 A1 Feb. 7, 2019

(30) Foreign Application Priority Data

Sep. 5, 2016 (CN) .......................... 2016 1 0802844

(51) Int. Cl.
*C12P 17/04* (2006.01)
*C12R 1/645* (2006.01)

(52) U.S. Cl.
CPC .............. *C12P 17/04* (2013.01); *C12R 1/645* (2013.01)

(58) Field of Classification Search
None
See application file for complete search history.

(56) References Cited

U.S. PATENT DOCUMENTS

| 2015/0259706 A1 | 9/2015 | Tsuchida et al. |
| 2018/0273915 A1* | 9/2018 | Tassone ............... C12N 9/0006 |

FOREIGN PATENT DOCUMENTS

| CN | 101434912 | 5/2009 |
| CN | 102242071 | 11/2011 |
| CN | 102643757 | 8/2012 |

* cited by examiner

*Primary Examiner* — Christian L Fronda
(74) *Attorney, Agent, or Firm* — JMB Davis Ben-David

(57) ABSTRACT

A yeast strain and a method for the synthesis of 2,5-dihydroxymethylfuran using this strain are disclosed. The yeast strain is *Meyerozyma guilliermondii* SC 1103, which has been maintained in the China Center for Type Culture Collection (CCTCC, Wuhan, P.R. China) with an access No. of M2016144. The method for the synthesis of 2,5-dihydroxymethylfuran using this strain is described as follows: after pre-cultivation and cultivation, *Meyerozyma guilliermondii* SC 1103 cells are added into the buffer solutions containing 5-hydroxymethylfurfural and glucose; the biocatalytic reaction is conducted under designated conditions, thus affording 2,5-dihydroxymethylfuran. This disclosure has many advantages such as good selectivity, mild reaction conditions, environmental friendliness, high efficiency, and good yield.

9 Claims, 2 Drawing Sheets

STRAIN OF MEYEROZYMA GUILLIERMONDII AND ITS USE IN METHODS OF CATALYTIC SYNTHESIS OF 2,5-DIHYDROXYMETHYLFURAN

CROSS REFERENCE OF PROVISIONAL APPLICATION

This is the U.S. National Stage of International Application No. PCT/CN2016/110022 filed Dec. 15, 2016, which was published in Chinese under PCT Article 21(2), and which in turn claims the benefit of priority from Provisional R.P. China Patent Application CN201610802844.7 filed on Sep. 5, 2016, the entire contents of which are incorporated by reference herein.

TECHNICAL FIELD

The disclosure relates to the field of biocatalysis and chemical engineering, and in particular relates to a yeast strain and a method for the catalytic synthesis of 2,5-dihydroxymethylfuran via 5-hydroxymethylfurfural reduction by this strain thereof.

BACKGROUND

In recent years, the synthesis and application of bio-based fuels and platform chemicals have attracted growing interest. 5-Hydroxymethylfurfural (HMF) was recognized by the U.S. Department of Energy (DOE) as one of "Top 10+4" bio-based chemicals (Green Chem., 2010, 12, 539). This bio-based platform chemical can be prepared via hexose dehydration of carbohydrates. HMF could be upgraded facilely into various useful chemicals, due to the presence of active groups such as primary hydroxyl and formyl. HMF could be transformed into 2,5-dihydroxymethylfuran (DHMF), 2,5-dihydroxymethyltetrahydrofuran (DHMTHF), 2,5-dimethylfuran (DMF) and 2,5-dimethyltetrahydrofuran (DMTHF) through selective reduction, and their structures were shown in FIG. 1. These reduced products were important fuel additives as well as building blocks, which have broad applications in fuel, medicine and polymer industries. For example, DHMF is a versatile building block for the synthesis of drugs and crown ethers (J. Am. Chem. Soc., 1974, 96, 7159) as well as bio-based polymers with multi-shape memory and self-healing ability (Macromolecules, 2013, 46, 1794; ACS Appl. Mater. Interfaces, 2014, 6, 2753).

To date, DHMF was synthesized mainly via chemical methods. For example, Cottier et al. described DHMF synthesis via stoichiometric reduction of HMF using two equivalents of sodium borohydride at 4° C.; DHMF was achieved in a yield of 97% (Synth. Commun., 2003, 33, 4285). Alamillo et al. reported HMF reduction over CeOx-supported Ru at 130° C.; after 2 h, HMF was transformed completely, and DHMF was obtained in a yield of 81% (Green Chem., 2012, 14, 1413). Ohyama et al. reported a gold sub-nano cluster supported on $Al_2O_3$ catalyzed hydrogenation of HMF at 120° C. with 6.5 MPa $H_2$, affording DHMF in the yield of 96% (RSC Adv., 2013, 3, 1033). Lin et al. described catalytic transfer hydrogenation of HMF to DHMF over low-cost $ZrO(OH)_2$ at 150° C.; after 2.5 h, the conversion of HMF was up to 94%, and the selectivity toward DHMF was 89% (Green Chem. 2016, 18, 1080).

Although significant progress in the chemical synthesis of DHMF was achieved, chemical methods suffered from harsh reaction conditions, unsatisfactory selectivity, and use of toxic catalysts and organic solvents and stoichiometric reductants, etc. Recently, biocatalysis has received increasing attention in both industry and academia, because the problems described above can be overcome. Nonetheless, biocatalytic reduction of HMF to DHMF remains challenging, due to the following facts: (1) to continuously shift the reaction toward reduction, stoichiometric costly cofactors NAD(P)H or complex regeneration systems of cofactors were required in alcohol dehydrogenase-mediated reduction of HMF; (2) although using microbial whole cells as biocatalysts is well able to overcome the above problem of coenzyme recycling, the substrate HMF is a well-known potent inhibitor to microorganisms, which exerts strong inhibitory effects on microorganisms (Bioresour. Technol., 2000, 74, 25); as a result, microorganisms generally show poor tolerance to HMF, and low reaction rates and so on. Although the HMF transformations catalyzed by microbial cells have been reported, their main objective is to biologically detoxify lignocellulosic acid hydrolysates, where microorganisms transformed the inhibitor HMF present in lignocellulosic hydrolysates into the low-toxicity compounds (Appl. Microbiol. Biotechnol., 2004, 64, 125). However, these microorganisms could not meet the requirements of biocatalysts for efficient synthesis of DHMF from HMF, because of the following reasons: (1) their biodetoxification efficiencies remained low, suggesting that HMF reduction rates were low; for instance, Lopez et al. found that complete transformation of HMF of a low concentration (15 mM) using *Coniochaeta ligniaria* NRRL 30616 required the period of 70 h (Appl. Microbiol. Biotechnol., 2004, 64, 125). Zhang et al. reported a strain *Enterobacter* sp. FDS8 which exhibited high efficiency in HMF degradation; nonetheless, the HMF concentration tested (3.2 mM) was pretty low (Biochem. Eng. J., 2013, 72, 77). (2) Their tolerance to HMF, especially that of high concentrations, was poor (Biotechnol. Biofuels, 2014, 7, 51). According to the previous reports in the literature, HMF would exert a significantly deleterious effect on biotransformations when the concentrations of HMF were high (Biotechnol. Biofuels, 2015, 78, 63). (3) The selectivities were not satisfactory; for example, Feldman et al. reported that *Pleurotus ostreatus* could completely transform 30 mM HMF within 48 h, but the products contained both the reduced derivative DHMF and the oxidized derivative 2,5-furandicarboxylic acid (Biotechnol. Biofuels, 2015, 78, 63). Therefore, microorganisms that are tolerant to high concentrations of HMF and have high activities and selectivities are critical to constructing an efficient biocatalytic approach to DHMF from HMF.

SUMMARY OF THE DISCLOSURE

To overcome the disadvantages inherent in the prior art, this disclosure provides a yeast strain (*Meyerozyma guilliermondii* SC 1103) which is highly tolerant to HMF, and shows good efficiency and selectivity in HMF reduction to DHMF as well as a method for the synthesis of DHMF using this yeast strain.

The aim of the present invention can be achieved by the following technical solutions: The yeast strain is *Meyerozyma guilliermondii* SC 1103, whose colonies have smooth humid and oyster white surfaces with a homogeneous structure, as shown in FIG. 2.

A method for the catalytic synthesis of 2,5-dihydroxymethylfuran using this yeast strain includes the following steps:

(1) pre-cultivating and cultivating the *Meyerozyma guilliermondii* SC 1103 in the liquid medium, followed by harvesting the yeast cells;

(2) adding the above-harvested yeast cells into buffer solutions containing 5-hydroxymethylfurfural and glucose, where the 5-hydroxymethylfurfural concentrations are 10-200 mM, and the glucose concentrations are 10-200 mM; conducting the reactions under 10-40° C., and thus affording 2,5-dihydroxymethylfuran.

In the first step, the liquid medium is the yeast extract peptone dextrose (YPD) medium containing 1% yeast extract, 2% peptone and 2% glucose; the conditions for pre-cultivation and cultivation are 30° C. and 200 r/min; the pre-cultivated seed culture of 2% was inoculated to the fresh YPD medium for subsequent cultivation.

The yeast cell concentrations are 10-30 mg/mL in the second step.

The 5-hydroxymethylfurfural concentrations are 20-110 mM, and the glucose concentrations are 10-100 mM in the second step.

The 5-hydroxymethylfurfural concentrations are 20-40 mM, and the glucose concentrations are 30-100 mM in the second step.

The buffer solutions are citrate, phosphate, Tris-HCl, or glycine-NaOH buffers, and pH of the buffer varies from 4.0 to 10.0 in the second step.

The reaction temperature varies from 20 to 35° C., and the rotation speed is 200 r/min in the second step.

In the second step, 2,5-dihydroxymethylfuran is synthesized via a fed-batch strategy for accumulating the product of a high concentration in the reaction mixture.

The steps of the fed-batch strategies include: monitoring the reaction time courses by the high-performance liquid chromatography; supplementing 5-hydroxymethylfurfural and glucose into the reaction mixture when 5-hydroxymethylfurfural is almost used up and then continuing the reaction; repeatedly conducting the above supplementation for accumulating 2,5-dihydroxymethylfuran of a high concentration.

Compared to previous methods, the present invention has advantages as follows:

(1) With *Meyerozyma guilliermondii* SC 1103 as biocatalyst, HMF can be efficiently and selectively transformed into DHMF, and the disadvantages of chemical methods such as environmental unfriendliness can be overcome.

(2) The reaction mixture is simple, because no nitrogen sources and mineral salts were added (the addition of extra chemicals would make the reaction system more complicated). The process is easily controlled, and the reaction conditions are mild. So side reactions cannot occur readily during the reduction of active HMF. It not only results in the improved product quality and the reduced energy consumption, but also favors the isolation and purification of the target product.

(3) With microbial cells as the catalyst, the cells can be recovered readily through centrifugation after the reaction, thus allowing the biocatalyst reusable and making the product purification easy.

The strain in the present invention is *Meyerozyma guilliermondii* SC 1103, which has been maintained on Mar. 31, 2016 in the China Center for Type Culture Collection, referred to CCTCC, with an access No. of M2016144. Its address is Wuhan University, Wuhan, P. R. China.

DESCRIPTION OF EXAMPLE EXAMPLES OF THE INVENTION

The present invention will be further described in detail below with reference to examples and figures; however, the examples of the present invention are not limited thereto.

Example 1

Pre-cultivation and cultivation of *Meyerozyma guilliermondii* SC 1103 cells *M. guilliermondii* SC1103 cells were pre-cultivated at 30° C. and 200 r/min for 12 h in the YPD medium containing 1% yeast extract, 2% peptone and 2% glucose. Then, 2% seed culture was inoculated to the fresh YPD medium. After incubation at 30° C. and 200 r/min for 12 h, the yeast cells were harvested.

Example 2

Figure 1:
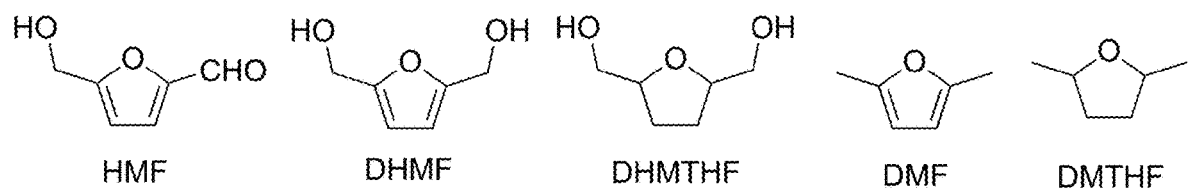
FIG. 1 shows the structures of HMF and its reduced derivatives.
Figure 2:
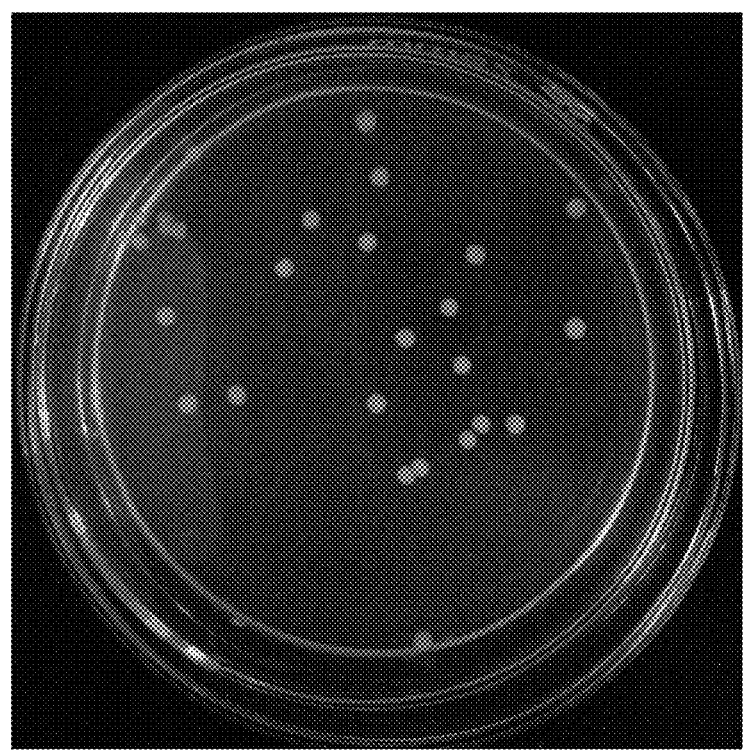
FIG. 2 shows the colonial morphology of *Meyerozyma guilliermondii* SC 1103 which grew on YPD agar medium with pH 6.5 under 30° C. for 3 days.
Figure 3:
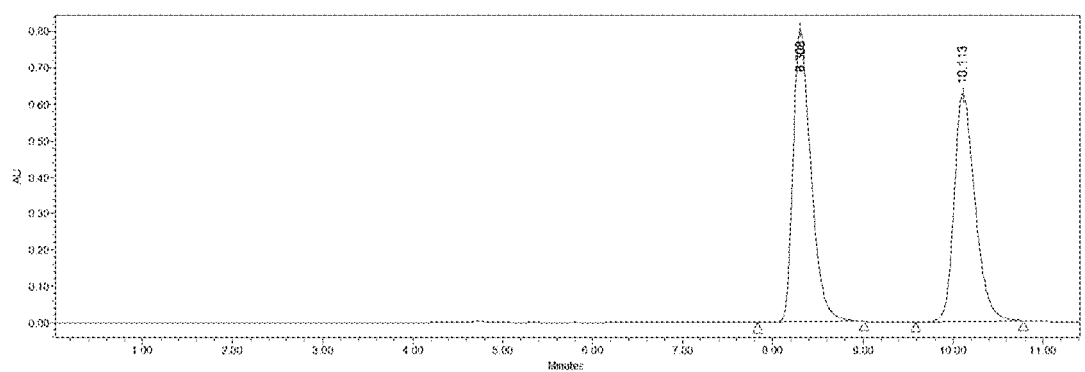
FIG. 3 shows HPLC spectrum of the reaction mixtures (the retention times of DHMF and HMF are 8.3 and 10.1 min, respectively).

To 4 mL of phosphate buffer (100 mM, pH 7.2), 0.16 mmol HMF and 0.12 mmol glucose were added and mixed evenly. Then *M. guilliermondii* SC1103 cells harvested in Example 1 were added with a concentration of 20 mg/mL (cell wet weight). The reaction mixture was incubated at 30° C. and 200 r/min. The biocatalytic reduction reaction was monitored by HPLC (FIG. 3). After 7 h, DHMF was afforded in a yield of 89% and a selectivity of 99%.

Example 3

To 4 mL of citrate buffer (100 mM, pH 4.0), 0.16 mmol HMF and 0.12 mmol glucose were added and mixed evenly. Then *M. guilliermondii* SC1103 cells harvested in Example 1 were added with a concentration of 20 mg/mL (cell wet weight). The reaction mixture was incubated at 30° C. and 200 r/min. After 7 h, DHMF was afforded in a yield of 89% and a selectivity of 99%.

Example 4

To 4 mL of glycine-NaOH buffer (100 mM, pH 10.0), 0.16 mmol HMF and 0.12 mmol glucose were added and mixed evenly. Then *M. guilliermondii* SC1103 cells harvested in Example 1 were added with a concentration of 20 mg/mL (cell wet weight). The reaction mixture was incubated at 30° C. and 200 r/min After 5 h, DHMF was afforded in a yield of 90% and a selectivity of 99%.

Example 5

To 4 mL of phosphate buffer (100 mM, pH 7.2), 0.16 mmol HMF and 0.12 mmol glucose were added and mixed evenly. Then *M. guilliermondii* SC1103 cells harvested in Example 1 were added with a concentration of 10 mg/mL (cell wet weight). The reaction mixture was incubated at 30° C. and 200 r/min After 9 h, DHMF was afforded in a yield of 91% and a selectivity of 98%.

Example 6

To 4 mL of phosphate buffer (100 mM, pH 7.2), 0.16 mmol HMF and 0.12 mmol glucose were added and mixed evenly. Then *M. guilliermondii* SC1103 cells harvested in Example 1 were added with a concentration of 30 mg/mL (cell wet weight). The reaction mixture was incubated at 30° C. and 200 r/min After 5 h, DHMF was afforded in a yield of 91% and a selectivity of 99%.

Example 7

To 4 mL of phosphate buffer (100 mM, pH 7.2), 0.16 mmol HMF and 0.12 mmol glucose were added and mixed evenly. Then *M. guilliermondii* SC1103 cells harvested in Example 1 were added with a concentration of 20 mg/mL (cell wet weight). The reaction mixture was incubated at 20° C. and 200 r/min After 24 h, DHMF was afforded in a yield of 93% and a selectivity of 99%.

Example 8

To 4 mL of phosphate buffer (100 mM, pH 7.2), 0.16 mmol HMF and 0.12 mmol glucose were added and mixed evenly. Then *M. guilliermondii* SC1103 cells harvested in Example 1 were added with a concentration of 20 mg/mL (cell wet weight). The reaction mixture was incubated at 40° C. and 200 r/min After 5 h, DHMF was afforded in a yield of 86% and a selectivity of 99%.

Example 9

To 4 mL of phosphate buffer (100 mM, pH 7.2), 0.08 mmol HMF and 0.12 mmol glucose were added and mixed evenly. Then *M. guilliermondii* SC1103 cells harvested in Example 1 were added with a concentration of 20 mg/mL (cell wet weight). The reaction mixture was incubated at 35° C. and 200 r/min After 3 h, DHMF was afforded in a yield of 93% and a selectivity of 99%.

Example 10

To 4 mL of phosphate buffer (100 mM, pH 7.2), 0.4 mmol HMF and 0.4 mmol glucose were added and mixed evenly. Then *M. guilliermondii* SC1103 cells harvested in Example 1 were added with a concentration of 20 mg/mL (cell wet weight). The reaction mixture was incubated at 35° C. and 200 r/min After 12 h, DHMF was afforded in a yield of 86% and a selectivity of 99%.

Example 11

To 4 mL of phosphate buffer (100 mM, pH 7.2), 0.44 mmol HMF and 0.4 mmol glucose were added and mixed evenly. Then *M. guilliermondii* SC1103 cells harvested in Example 1 were added with a concentration of 20 mg/mL (cell wet weight). The reaction mixture was incubated at 35° C. and 200 r/min After 36 h, DHMF was afforded in a yield of 87% and a selectivity of 99%.

Example 12

To 4 mL of phosphate buffer (100 mM, pH 7.2), 0.6 mmol HMF and 0.4 mmol glucose were added and mixed evenly. Then *M. guilliermondii* SC1103 cells harvested in Example 1 were added with a concentration of 20 mg/mL (cell wet weight). The reaction mixture was incubated at 35° C. and 200 r/min After 48 h, DHMF was afforded in a yield of 51% and a selectivity of 99%.

Example 13

To 4 mL of phosphate buffer (100 mM, pH 7.2), 0.8 mmol HMF and 0.8 mmol glucose were added and mixed evenly. Then *M. guilliermondii* SC1103 cells harvested in Example 1 were added with a concentration of 20 mg/mL (cell wet weight). The reaction mixture was incubated at 35° C. and 200 r/min After 48 h, DHMF was afforded in a yield of 42% and a selectivity of 99%.

Example 14

Synthesis of DHMF Via a Fed-Batch Strategy

To 4 mL of phosphate buffer (100 mM, pH 7.2), 0.2 mmol HMF and 0.12 mmol glucose were added and mixed evenly. Then *M. guilliermondii* SC1103 cells harvested in Example 1 were added with a concentration of 20 mg/mL (cell wet weight). The reaction mixture was incubated at 35° C. and 200 r/min. After 6 h, the concentrations of HMF and DHMF in the reaction mixture was changed to 1.8 mM and 46.1 mM, respectively; 0.2 mmol HMF and 0.12 mmol glucose were supplemented. The reaction was conducted under the above conditions for further 7 h. The HMF and DHMF concentrations in the mixture were 2.8 and 88.7 mM, respectively. Then 0.2 mmol HMF and 0.12 mmol glucose were supplemented. The HMF and DHMF concentrations in the mixture were 6.1 and 132.1 mM, respectively, after reaction for 5 h. Then 0.2 mmol HMF and 0.12 mmol glucose were supplemented again. After 6.5 h, the concentration of DHMF increased to 190.6 mM in the reaction mixture, while the HMF concentration decreased to 2.4 mM. DHMF was obtained with the total yield of up to 95% and the selectivity of 99%.

Comparative Example 1

To 4 mL of phosphate buffer (100 mM, pH 7.2), 40 mM HMF, 30 mM glucose, 2 g/L $(NH_4)_2SO_4$ and mineral salts (0.1 g/L $MgCl_2.6H_2O$, 10 mg/L EDTA, 2 mg/L $ZnSO_4.7H_2O$, 1 mg/L $CaCl_2.2H_2O$, 5 mg/L $FeSO_4.7H_2O$, 0.2 mg/L $Na_2MoO_4.2H_2O$, 0.2 mg/L $CuSO_4.5H_2O$, 0.4 mg/L $CoCl_2.6H_2O$ and 1 mg/L $MnCl_2.2H_2O$) were added and mixed evenly. Then *M. guilliermondii* SC1103 cells harvested in Example 1 were added with a concentration of 20 mg/mL (cell wet weight). The reaction mixture was incubated at 30° C. and 200 r/min. After 7 h, DHMF was afforded in a yield of 88% and a selectivity of 99%.

Comparative Example 2

To 4 mL of phosphate buffer (100 mM, pH 7.2), 40 mM HMF, 30 mM glycerol, 2 g/L $(NH_4)_2SO_4$ and mineral salts (0.1 g/L $MgCl_2.6H_2O$, 10 mg/L EDTA, 2 mg/L $ZnSO_4.7H_2O$, 1 mg/L $CaCl_2.2H_2O$, 5 mg/L $FeSO_4.7H_2O$, 0.2 mg/L $Na_2MoO_4.2H_2O$, 0.2 mg/L $CuSO_4.5H_2O$, 0.4 mg/L $CoCl_2.6H_2O$ and 1 mg/L $MnCl_2.2H_2O$) were added and mixed evenly. Then *M. guilliermondii* SC1103 cells harvested in Example 1 were added with a concentration of 20 mg/mL (cell wet weight). The reaction mixture was incubated at 30° C. and 200 r/min After 24 h, DHMF was afforded in a yield of 88% and a selectivity of 93%.

Comparative Example 3

To 4 mL of phosphate buffer (100 mM, pH 7.2), 40 mM HMF, 15 mM glucose, 2 g/L $(NH_4)_2SO_4$ and mineral salts (0.1 g/L $MgCl_2.6H_2O$, 10 mg/L EDTA, 2 mg/L $ZnSO_4.7H_2O$, 1 mg/L $CaCl_2.2H_2O$, 5 mg/L $FeSO_4.7H_2O$, 0.2 mg/L $Na_2MoO_4.2H_2O$, 0.2 mg/L $CuSO_4.5H_2O$, 0.4 mg/L $CoCl_2.6H_2O$ and 1 g/L $MnCl_2.2H_2O$) were added mixed evenly. Then *M. guilliermondii* SC1103 cells harvested in Example 1 were added with a concentration of 20 mg/mL (cell wet weight). The reaction mixture was incubated at 30° C. and 200 r/min After 12 h, DHMF was afforded in a yield of 88% and a selectivity of 98%.

Comparative Example 4

To 4 mL of phosphate buffer (100 mM, pH 7.2), 40 mM HMF, 2 g/L $(NH_4)_2SO_4$ and mineral salts (0.1 g/L $MgCl_2.6H_2O$, 10 mg/L EDTA, 2 mg/L $ZnSO_4.7H_2O$, 1 mg/L $CaCl_2.2H_2O$, 5 mg/L $FeSO_4.7H_2O$, 0.2 mg/L $Na_2MoO_4.2H_2O$, 0.2 mg/L $CuSO_4.5H_2O$, 0.4 mg/L $CoCl_2.6H_2O$ and 1 mg/L $MnCl_2.2H_2O$) were added and mixed evenly. Then *M. guilliermondii* SC1103 cells harvested in Example 1 were added with a concentration of 20 mg/mL (cell wet weight). The reaction mixture was incubated at 30° C. and 200 r/min After 24 h, DHMF was afforded in a yield of 55% and a selectivity of 61%.

Comparative Example 5

To 4 mL of phosphate buffer (100 mM, pH 7.2), 40 mM HMF, 30 mM glucose and mineral salts (0.1 g/L $MgCl_2.6H_2O$, 10 mg/L EDTA, 2 mg/L $ZnSO_4.7H_2O$, 1 mg/L $CaCl_2.2H_2O$, 5 mg/L $FeSO_4.7H_2O$, 0.2 mg/L $Na_2MoO_4.2H_2O$, 0.2 mg/L $CuSO_4.5H_2O$, 0.4 mg/L $CoCl_2.6H_2O$ and 1 mg/L $MnCl_2.2H_2O$) were added and mixed evenly. Then *M. guilliermondii* SC1103 cells harvested in Example 1 were added with a concentration of 20 mg/mL (cell wet weight). The reaction mixture was incubated at 30° C. and 200 r/min After 7 h, DHMF was afforded in a yield of 91% and a selectivity of 99%.

Comparative Example 6

To 4 mL of phosphate buffer (100 mM, pH 7.2), 40 mM HMF, 30 mM glucose and 2 g/L $Na_2SO_4$ were added and mixed evenly. Then *M. guilliermondii* SC1103 cells harvested in Example 1 were added with a concentration of 20 mg/mL (cell wet weight). The reaction mixture was incubated at 30° C. and 200 r/min After 7 h, DHMF was afforded in a yield of 86% and a selectivity of 99%.

What is claimed is:

1. A yeast strain, characterized in that said yeast strain is *Meyerozyma guilliermondii* SC 1103 which has been maintained on Mar. 31, 2016 in the China Center for Type Culture Collection referred to as CCTCC with an access No. of M2016144.

2. A method for the catalytic synthesis of 2,5-dihydroxymethylfuran comprising:
   (1) pre-cultivating and cultivating the yeast strain of claim 1, in liquid medium, followed by harvesting the yeast cells;
   (2) adding the harvested yeast cells into buffer solutions containing 5-hydroxymethylfurfural and glucose to produce a reaction mixture, where the 5-hydroxymethylfurfural concentrations are 10-200 mM, and the glucose concentrations are 10-200 mM; and incubating the reaction mixture at 10-40° C., thereby producing 2,5-dihydroxymethylfuran.

3. The method according to claim 2, wherein the yeast cell concentrations are 10-30 mg/mL in the second step.

4. The method according to claim 3, wherein the 5-hydroxymethylfurfural concentrations are 20-110 mM, and the glucose concentrations are 10-100 mM in the second step.

5. The method according to claim 4, wherein the 5-hydroxymethylfurfural concentrations are 20-100 mM, and the glucose concentrations are 30-100 mM in the second step.

6. The method according to claim 5, wherein the buffer solutions are citrate, phosphate, Tris-HCl, or glycine-NaOH buffers, and pH of the buffer varies from 4.0 to 10.0 in the second step.

7. The method according to claim 6, wherein reaction temperature varies from 20 to 35° C., and the rotation speed is 200 r/min in the second step.

8. The method according to claim 2, wherein 2,5-dihydroxymethylfuran is synthesized via a fed-batch strategy for accumulating the product of a high concentration in the reaction mixture in the second step.

9. The method according to claim 8, wherein the steps of the fed-batch strategies include: monitoring the reaction time courses by the high performance liquid chromatography; supplementing 5-hydroxymethylfurfural and glucose into the reaction mixture when 5-hydroxymethylfurfural is almost used up and then continuing the reaction; repeatedly conducting the above supplementation for accumulating 2,5-dihydroxymethylfuran of a high concentration.

* * * * *